(12) United States Patent
Kawasaki

(10) Patent No.: US 7,146,746 B2
(45) Date of Patent: Dec. 12, 2006

(54) METHOD OF DECONTAMINATION AND DECONTAMINATION APPARATUS

(75) Inventor: Koji Kawasaki, Nagoya (JP)

(73) Assignee: Airex Co., Ltd., Aichi (JP)

( * ) Notice: Subject to any disclaimer, the term of this patent is extended or adjusted under 35 U.S.C. 154(b) by 0 days.

(21) Appl. No.: 11/381,903

(22) Filed: May 5, 2006

(65) Prior Publication Data

US 2006/0185189 A1    Aug. 24, 2006

Related U.S. Application Data

(63) Continuation of application No. PCT/JP2004/015778, filed on Oct. 25, 2004.

(51) Int. Cl.
*F26B 3/00* (2006.01)

(52) U.S. Cl. ............... 34/352; 159/2.1; 422/34

(58) Field of Classification Search ............... 34/352, 34/361, 380, 381, 77, 78, 90, 80; 159/2.1; 422/34; 134/1

See application file for complete search history.

(56) References Cited

U.S. PATENT DOCUMENTS

| | | | | |
|---|---|---|---|---|
| 3,767,362 A | * | 10/1973 | Griffin et al. | 422/27 |
| 5,261,965 A | * | 11/1993 | Moslehi | 134/1 |
| 5,464,580 A | * | 11/1995 | Popescu et al. | 422/34 |
| 6,290,906 B1 | * | 9/2001 | MacNeal | 422/30 |
| 6,451,254 B1 | | 9/2002 | Wang et al. | |

2004/0001774 A1    1/2004    Williams et al.

FOREIGN PATENT DOCUMENTS

| | | |
|---|---|---|
| GB | 2 127 692 A | 4/1984 |
| JP | 61-4543 | 2/1986 |
| JP | 2000-217893 | 8/2000 |
| JP | 2004-160183 | 6/2004 |

OTHER PUBLICATIONS

International Search Report for PCT/JP2004/015778 mailed Feb. 8, 2005.

* cited by examiner

*Primary Examiner*—S. Gravini
(74) *Attorney, Agent, or Firm*—Darby & Darby

(57) ABSTRACT

A method of decontamination includes generating a decontamination gas by evaporating an aqueous solution in which the decontamination gas with a higher boiling point than water is dissolved. The decontamination gas is charged into a hermetically sealed decontamination chamber, and then condensed therein. A condensed liquid layer is formed in a form of a thin film on an outer surface of a decontamination subject in the hermetically sealed decontamination chamber. The condensed liquid layer is evaporated at least partially by supplying unsaturated gas into the hermetically sealed decontamination chamber. The unsaturated gas does not saturate in the hermetically sealed decontamination chamber. The decontamination gas is re-condensed after the evaporating step to re-form the condensed liquid layer, by closing supply of the unsaturated gas and re-charging the decontamination gas into the hermetically sealed decontamination chamber.

14 Claims, 7 Drawing Sheets

METHOD OF DECONTAMINATION AND DECONTAMINATION APPARATUS

CROSS-REFERENCE TO RELATED APPLICATION

This application is a Continuation of International Patent Application No. PCT/JP2004/015778, filed Oct. 25, 2004, and claims the benefit of Japanese Patent Application Nos 2003-383967, filed Nov. 13, 2003 and 2004-016932, filed Jan. 26, 2004, all of which are incorporated by reference herein. The International Application was published in Japanese on May 26, 2005 as WO 2005/046742 A1 under PCT Article 21(2).

BACKGROUND OF THE INVENTION

1. Field of the Invention

The present invention relates to a decontamination method for decontaminating a hermetically sealed decontamination chamber and a decontamination subject placed inside the hermetically sealed decontamination chamber, and a decontamination apparatus.

2. Background of the Invention

There are several conventional methods for decontaminating hermetically sealed decontamination chambers and decontamination subjects (empty syringe outer tubes used for producing pre-filled syringes, and the like) placed in the hermetically sealed decontamination chambers. For example, using a gas generating apparatus, hydrogen peroxide gas is generated; this hydrogen peroxide gas is charged in the hermetically sealed decontamination chamber; the room temperature of the hermetically sealed decontamination chamber is lowered to saturate the hermetically sealed decontamination chamber; and a thin film of a condensed liquid layer of hydrogen peroxide is formed on the inner wall of the hermetically sealed decontamination chamber and the outer surface of the decontamination subject (e.g., see in general Japanese Laid Open Patent Application No. S61-4543). Furthermore, the higher the hydrogen peroxide concentration for this condensed liquid layer, the higher the decontamination effect. The decontamination described above includes chemical decontamination, sterilization, disinfection, and the like.

However, according to the conventional method described above, the concentration of hydrogen peroxide in the condensed liquid layer, once it has been formed, decreases as time passes, and the decontamination effect is lowered. This is for the following reason. Because the hydrogen peroxide contained in aqueous hydrogen peroxide has a higher boiling point than water, when the room temperature of the hermetically sealed decontamination chamber is lowered and the condensed liquid layer is formed, the hydrogen peroxide begins to condense first to form the liquid layer, and then afterwards water vapor begins to condense. In other words, in the initial stage of the process of condensation, a condensed liquid layer with a high hydrogen peroxide concentration is formed, but after a certain amount of time, the water vapor begins to condense, and the overall hydrogen peroxide concentration is lowered. For example, by evaporating 35% aqueous hydrogen peroxide to generate hydrogen peroxide gas, in the initial period of the condensation process, a condensed liquid layer with a concentration of 58% is formed. However, after a certain amount of time, the concentration is reduced to near 35%.

SUMMARY OF THE INVENTION

The object of the present invention is to provide a method of decontamination and decontamination apparatus in which, when forming a condensed liquid layer by condensing hydrogen peroxide gas, the decontamination effectiveness is not reduced with the passage of time.

According to one aspect of the present invention, a method of decontamination includes generating a decontamination gas by evaporating an aqueous solution in which the decontamination gas with a higher boiling point than water is dissolved. The decontamination gas is charged into a hermetically sealed decontamination chamber. The decontamination gas is condensed in the hermetically sealed decontamination chamber. A condensed liquid layer is formed in a form of a thin film on an outer surface of a decontamination subject in the hermetically sealed decontamination chamber. The condensed liquid layer is evaporated at least partially by supplying unsaturated gas into the hermetically sealed decontamination chamber. The unsaturated gas does not saturate in the hermetically sealed decontamination chamber. The decontamination gas is re-condensed after the evaporating step to re-form the condensed liquid layer. The decontamination gas is re-condensed by closing supply of the unsaturated gas and re-charging the decontamination gas into the hermetically sealed decontamination chamber.

Because the decontamination gas has a higher boiling point than water, in the initial stage during the process of condensation, a condensed liquid layer with a high solute concentration (the ratio of the weight, volume, mole number of the dissolved decontamination gas with respect to the overall solution volume) is formed. After forming the condensed liquid layer, the solute concentration starts to decrease. However, with the present invention, because there is an evaporation step for evaporating the condensed liquid layer which has been formed, the decrease in solute concentration is prevented. This is because, when the condensed liquid layer is evaporated, the water in the condensed liquid layer is vaporized before the condensed liquid of the decontamination gas. The condensed liquid of the decontamination gas remains in the condensed liquid layer, and the overall solute concentration of the condensed liquid layer is increased.

With regard to the modes for evaporating the condensed liquid layer, there is a mode for evaporation of the entire condensed liquid layer, and there is a mode for partial evaporation. If the condensed liquid layer that has formed is only partially evaporated, a condensed liquid layer of high concentration is formed. On the other hand, if the condensed liquid layer that has been formed is wholly evaporated, the decrease in concentration is stopped substantially completely.

Further, with the present invention, there is a re-condensation step for re-forming the condensed liquid layer. With this construction, a condensed liquid layer with a high concentration and a high decontamination effect is formed on the outer surface of the decontamination subject. Therefore, the condensed liquid layer maintains a high concentration and high decontamination effect for a longer period than the conventional method. Moreover, the condensed liquid layer is evaporated and re-formed without having to change the temperature or inner pressure of the hermetically sealed decontamination chamber. Accordingly, the decontamination time is shortened compared to the conventional method.

According to another aspect of the present invention, the method of decontamination includes providing a chamber with a chamber wall having a supply opening to supply a decontamination subject into the chamber, and a discharge opening to discharge the decontamination subject from the chamber after being decontaminated. The decontamination subject is supplied into the chamber through the supply opening. The supply opening and the discharge opening are closed to turn the chamber to a hermetically sealed decontamination chamber with the decontamination subject inside. Decontamination gas is charged into the hermetically sealed decontamination chamber. The decontamination gas is condensed in the hermetically sealed decontamination chamber. A condensed liquid layer is formed in a form of a thin film on an outer surface of the decontamination subject so as to decontaminate the decontamination subject.

Subsequently, the condensed liquid layer is evaporated at least partially by supplying unsaturated gas into the hermetically sealed decontamination chamber. The decontamination gas is re-condensed after the evaporating step to re-form the condensed liquid layer, by closing supply of the unsaturated gas and re-charging the decontamination gas into the hermetically sealed decontamination chamber. The condensed liquid layer re-formed on the outer surface of the decontamination subject is removed. Then, the decontamination subject is discharged through the discharge opening. Further, the forming step is performed during a first half of the steps beginning the supplying step and ending the discharging step. The evaporating step is performed when a predetermined period of time is passed after the condensed liquid layer is formed in the forming step. The removing step is performed during a second half of the steps beginning the supplying step and ending the discharging step.

In the conventional method, the decontamination gas was dispersed over the entirety of the hermetically sealed decontamination chamber. Afterwards, the decontamination gas dispersed over the entire chamber must be removed entirely (aeration). As a result, the decontamination time could be very long. However, in the present invention, because there is no need to disperse the decontamination gas over the entire region of the hermetically sealed decontamination chamber, the decontamination time is shortened as compared to the conventional method.

According to yet another aspect of the present invention, the decontamination apparatus includes a chamber, a decontamination gas supplying device, an unsaturated gas supplying device, a condensation controlling device, and a removing device. The chamber has a chamber wall provided with a supply opening to supply a decontamination subject into the chamber, and a discharge opening to discharge the decontamination subject from the chamber after being decontaminated. The chamber is turned to a hermetically sealed decontamination chamber when the supply opening and the discharge opening are closed. The decontamination gas supplying device is provided with a decontamination gas release opening facing oppositely to an outer surface of the decontamination subject in the chamber, and configured to release decontamination gas toward the decontamination subject through the decontamination gas release opening. The decontamination gas is generated by evaporating an aqueous solution in which the decontamination gas with a higher boiling point than water is dissolved.

Further, the unsaturated gas supplying device is provided with an unsaturated gas release opening facing oppositely to the outer surface of the decontamination subject, and configured to generate and release unsaturated gas toward the decontamination subject through the unsaturated gas release opening. The unsaturated gas does not saturate in the hermetically sealed decontamination chamber. The condensation controlling device is configured to condense the decontamination gas released in the hermetically sealed decontamination chamber, to form a condensed liquid layer in a form of a thin film on the outer surface of the decontamination subject, and to decontaminate the decontamination subject. The removing device is configured to remove the condensed liquid layer from the decontamination subject.

In the above aspect, the decontamination subject is decontaminated by a high concentration condensed liquid layer. After removing the condensed liquid layer, a decontaminated decontamination subject is effectively achieved.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
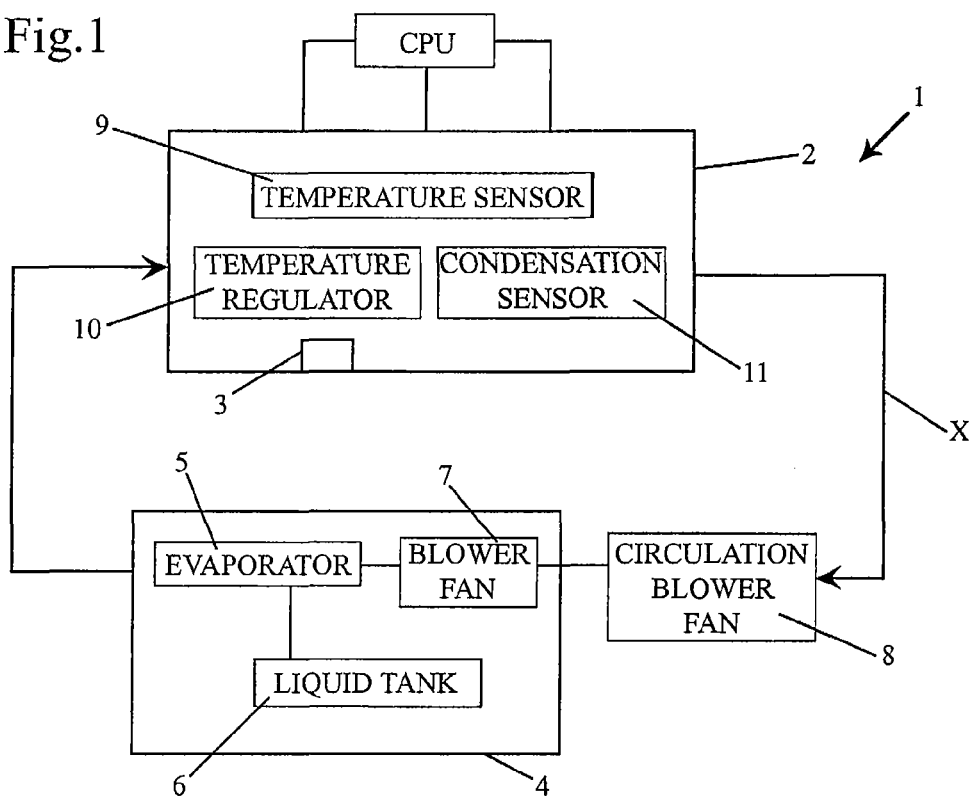
FIG. 1 is a schematic drawing of a decontamination apparatus according to an embodiment of the present invention.

The embodiments will now be described with reference to the accompanying drawings, wherein like reference numerals designate corresponding or identical elements throughout the various drawings.

FIG. 1 shows a schematic drawing of a decontamination apparatus 1. Referring to FIG. 1, the decontamination apparatus 1 decontaminates a chamber 2 (a hermetically sealed decontamination chamber) and a decontamination subject 3 placed inside chamber 2. The decontamination apparatus 1 uses hydrogen peroxide gas as the decontamination gas.

As shown in FIG. 1, the decontamination apparatus 1 is equipped with the chamber 2 and a gas generating apparatus 4. The chamber 2 forms a hermetically sealed space. In addition, the gas generating apparatus 4 generates hydrogen peroxide gas. From a circuit X, hydrogen peroxide gas from the gas generating apparatus 4 is charged in the chamber 2. With this circuit X, this is a circulating circuit, and gas inside the chamber 2 is sent again to the gas generating apparatus 4.

In addition, the inside chamber 2, there are provided a temperature sensor 9, a temperature regulator 10, and a condensation sensor 11. The temperature sensor 9 detects the room temperature inside the chamber 2. In addition, the temperature regulator 10 adjusts the room temperature inside the chamber 2. Furthermore, the condensation sensor 11 detects the presence or absence of a condensed liquid layer formed on the inner wall of the chamber 2 and outer surface of the decontamination subject 3. The temperature sensor 9, the temperature regulator 10, and the condensation sensor 11 are each electrically connected with a central control apparatus CPU. For the temperature sensor 9, the temperature regulator 10, and the condensation sensor 11, known examples are used.

The gas generating apparatus 4 is equipped with an evaporator 5, a liquid tank 6, and a blower fan 7. The evaporator 5 has a construction for generating gas by flash evaporation (so-called rapid evaporation method). In addition, inside the liquid tank 6, there is aqueous hydrogen peroxide in which hydrogen peroxide gas is dissolved. The aqueous hydrogen peroxide is dripped onto a heating surface (not shown) of the evaporator 5 by gravity and this is evaporated to generate hydrogen peroxide gas. In addition, the blower fan 7 sends the hydrogen peroxide gas that is generated into the chamber 2. For the gas generating apparatus 4, known examples are used.

In addition, a circulation blower fan 8 is provided on the circuit X. The circulation blower fan 8 is constantly circulating hydrogen peroxide gas inside the circuit X.

Next, the decontamination method using decontamination apparatus 1 is described.

First, hydrogen peroxide gas is generated using gas generating apparatus 4. Next, this hydrogen peroxide gas is charged in chamber 2. Next, the hydrogen peroxide gas is saturated inside chamber 2 and condensed. A thin film condensed liquid layer is formed on the outer surface of the inner wall of chamber 2 and decontamination subject 3. In order to condense hydrogen peroxide gas, the room temperature inside chamber 2 is lowered using temperature regulator 10 to make saturated conditions. When the condensed liquid layer is formed on the inner wall of chamber 2 and the outer surface of decontamination subject 3, a decontamination effect is achieved.

Furthermore, the present decontamination method implements an evaporation process in which the condensed liquid layer that is formed is partially evaporated. Stated more concretely, this is evaporated as follows. First, condensation sensor 11 detects the presence of a condensed liquid layer. Condensation sensor 11 sends a detection signal to a central control apparatus CPU. When central control apparatus CPU receives the detection signal, after a prescribed time has passed, a signal is sent to temperature regulator 10. This signal is for raising the room temperature. When temperature regulator 10 receives the signal, the room temperature of chamber 2 is raised to a prescribed temperature. With this, the condensed liquid layer that has been formed is partially evaporated. With this, the evaporation process is implemented.

In the process for evaporating the condensed liquid layer, of the water and hydrogen peroxide that is contained in the condensed liquid layer, the water vaporizes first. This is because the boiling point of water is lower than that of the boiling point of hydrogen peroxide (150 degrees C.). Therefore, when implementing an evaporation process which partially evaporates the condensed liquid layer, a condensed liquid layer with a high hydrogen peroxide concentration is formed on the outer surface of decontamination subject 3. The time from the receiving of the signal by temperature regulator 10 to the sending of the signal and the temperature for evaporating the condensed liquid layer is adjusted as appropriate.

Furthermore, in the present invention, a re-condensation process is implemented in which, after the evaporation process, the hydrogen peroxide gas is condensed again, and the condensed liquid layer is re-formed. Stated more concretely, re-formation is conducted as follows.

First, after a prescribed amount of time has passed from the implementation of the evaporation process, the central control apparatus CPU sends a signal to temperature regulator 10. This signal is a signal to lower the room temperature. With this, the hydrogen peroxide gas begins to re-condense, and a condensed liquid layer is formed again on the outer surface of decontamination subject 3 and the like. This is the implementation of the re-condensation process. When the re-formation of the condensed liquid layer is inadequate, hydrogen peroxide gas is newly charged while lowering the room temperature in the re-condensation process.

In the process of forming the condensed liquid layer again, as is already known, hydrogen peroxide gas condenses before water. Therefore, in the initial stage, a condensed liquid layer with a high hydrogen peroxide concentration is formed. The time from the implementation of the evaporation process to the sending of the signal for lowering the room temperature by the central control apparatus CPU and the temperature for forming the condensed liquid layer is set as appropriate.

This re-condensation process can be implemented a plurality of times. In other words, the evaporation and formation of the condensed liquid layer is conducted repeatedly. This is because the condensed liquid layer is essentially maintained at a high concentration for a long period of time, and the decontamination effect is dramatically improved. In addition, using temperature regulator 10 and central control apparatus CPU, and the like, there can be a construction in which the above temperature regulation is under automatic control. This results in a simpler management of the decontamination of chamber 2 and decontamination subject 3.

When condensation sensor 11 is of a construction which detects the layer thickness of the condensed liquid layer, the following construction is proposed. In other words, when condensation sensor 11 detects that the condensed liquid layer has reached a prescribed thickness, a detection signal is sent to the central control apparatus CPU. When central control apparatus CPU receives the detection signal, after a prescribed time has passed, a signal is sent to temperature regulator 10 to raise the room temperature, and the evaporation process is implemented. This construction specifies in advance the layer thickness for the condensed liquid layer with the highest decontamination effect, and the evaporation process is implemented according to the timing for this layer thickness.

Next, another embodiment is described.

Figure 2:
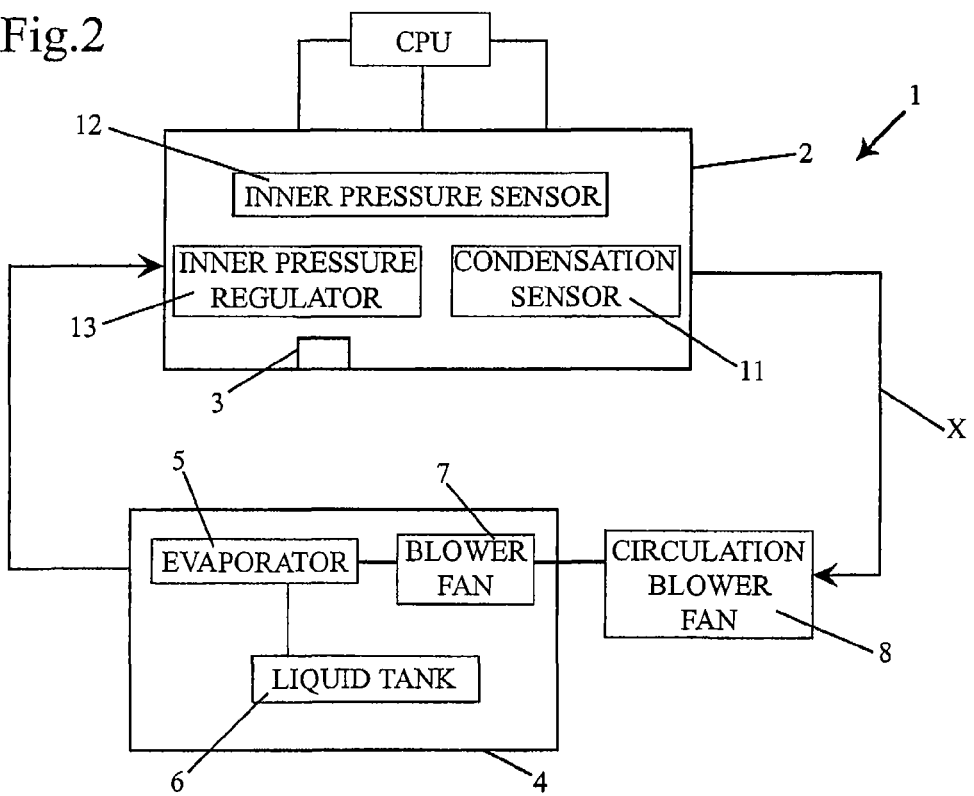
FIG. 2 is a schematic drawing of the decontamination apparatus provided with an inner pressure regulator.

As shown in FIG. 2, decontamination apparatus 1 has the construction of having an inner pressure sensor 12, an inner pressure regulator 13, and a condensation sensor 11. Inner pressure sensor 12 detects the inner pressure of chamber 2. In addition, inner pressure regulator 13 adjusts the inner pressure of chamber 2. Condensation sensor 11 has the same construction as described above. In addition, for inner pressure sensor 12 and inner pressure regulator 13, known examples are used.

Next, the decontamination method using the above embodiment is described.

First, hydrogen peroxide gas is charged in chamber 2. Next, the inner pressure of chamber 2 is raised (+10 to 1000 Pa). With this, the hydrogen peroxide gas becomes saturated inside chamber 2, and a condensed liquid layer is formed. Afterwards, after a prescribed amount of time has passed, central control apparatus CPU sends a signal to inner pressure regulator 13. This signal is a signal for lowering the inner pressure to a prescribed pressure. Inner pressure regulator 13 which receives this signal releases pressure to lower the inner pressure to the prescribed pressure. With this, a portion of the condensed liquid layer that has formed begins to evaporate. With this, the evaporation process is implemented, and the hydrogen peroxide concentration of the condensed liquid layer is increased, and the lowering of the concentration of the condensed liquid layer is prevented. Furthermore, afterwards, the inner pressure is raised to a prescribed pressure, and the condensed liquid layer is re-formed. With this, the re-condensation process is implemented, and a highly concentrated condensed liquid layer is again maintained on the surface of decontamination subject 3 and the like. The re-condensation process can be implemented a plurality of times. In addition, if the re-formation of the condensed liquid layer is inadequate, hydrogen peroxide gas can be charged while raising the inner pressure.

In addition, for a means for implementing the evaporation process and re-condensation process, the following embodiment is proposed. In other words, it is an embodiment which uses an unsaturated gas supply apparatus. The unsaturated gas supply apparatus supplies to the inside of chamber 2 unsaturated gas which does not become saturated inside chamber 2.

A decontamination method using the above embodiment is described.

First, hydrogen peroxide gas is charged in chamber 2, and a condensed liquid layer is formed. Next, using the unsaturated gas supply apparatus, unsaturated gas is supplied to inside chamber 2. When a certain amount of unsaturated gas is supplied, the inner pressure inside chamber 2 increases, and a portion of the condensed liquid layer begins to evaporate. With this, the evaporation process is implemented. Next, the supply of unsaturated gas is stopped, and the evaporation process is completed. Hydrogen peroxide gas is again charged, and the hydrogen peroxide gas is in a saturated condition inside chamber 2. With this, condensation of hydrogen peroxide gas is initiated, and the condensed liquid layer is re-formed. With this, the re-condensation process is implemented. The supply amount of unsaturated gas is prescribed as appropriate for implementing the evaporation process.

With the above embodiment, in order to evaporate and re-form hydrogen peroxide gas, the temperature and inner pressure inside chamber 2 does not need to be changed. As a result, the cycle for repeating the evaporation process and re-condensation process is implemented rapidly.

With the decontamination methods described thus far, when decontamination is completed, hydrogen peroxide gas from inside chamber 2 is removed (aeration).

With the decontamination apparatus 1 described thus far, it has a condensation method by pressurization. Compared to the conventional de-pressurization method, it is better for absolutely maintaining sterile conditions. With decontamination apparatus 1 described thus far, in addition to the embodiment described above, various embodiments may be added.

In addition, the embodiment described thus far has a construction for detecting the presence or absence of the condensed liquid layer by condensation sensor 11. However, the presence or absence of the condensed liquid layer may also be detected by a humidity sensor placed in chamber 2.

In addition, for the decontamination method, there can be an embodiment in which, in the evaporation process, the condensed liquid layer is wholly evaporated. If the condensed liquid layer is wholly evaporated, there is no decrease in concentration of the condensed liquid layer, and as a result, the decrease in concentration of the condensed liquid layer is completely prevented.

The condensation control means described in claims 14 and 15 is constructed by a central control apparatus CPU which condenses hydrogen peroxide gas inside chamber 2 and forms a condensed liquid layer as a thin film on the inner surface of chamber 2. In addition, the means for removing the condensed liquid layer is constructed by central control apparatus CPU which partially or wholly evaporates the condensed liquid layer. Furthermore, the re-condensation control means described in claims 14 and 15 is constructed by a central control apparatus CPU which, after evaporating the condensed liquid layer, condenses the hydrogen peroxide gas again to re-form the condensed liquid layer (includes a plurality of times).

According to another embodiment of the present invention, a decontamination apparatus 1a decontaminates a decontamination subject 3a which is a material 50 which has already been decontaminated and is wrapped in a wrapping material 51 while maintaining sterile conditions.

Figure 8:
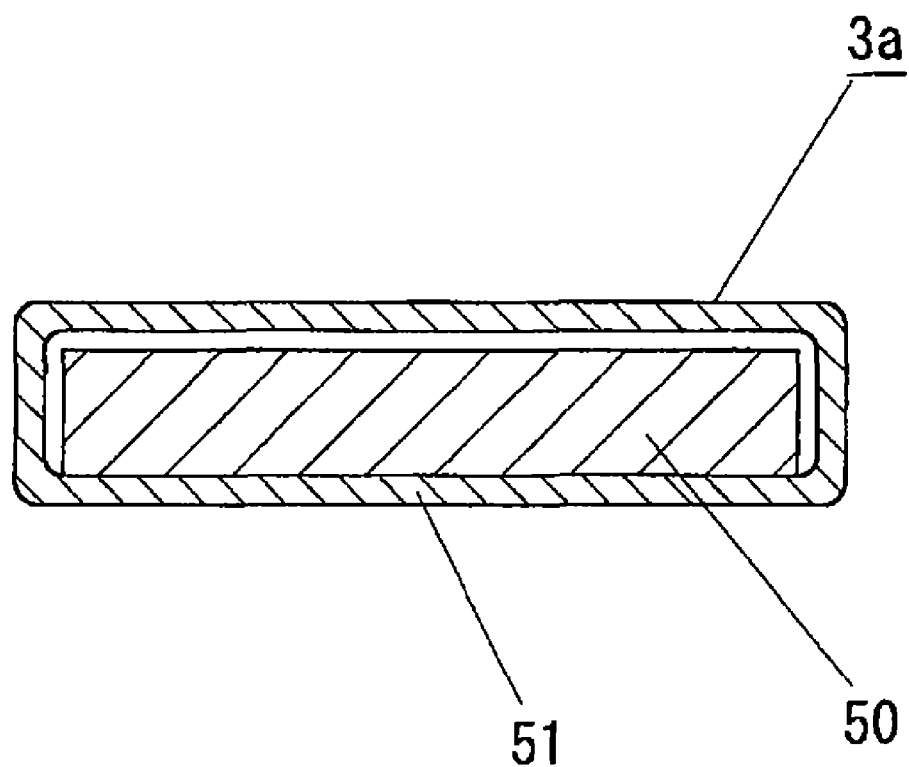
FIG. 8 is a longitudinal side view of the decontamination subject having material 50 and the wrapping material.

As shown in FIG. 8, decontamination subject 3a is a material 50 wrapped by a wrapping material 51. Material 50 has already been decontaminated. Material 50 is wrapped with wrapping material 51 while maintaining sterile conditions. In addition, wrapping material 51 has low permeability with respect to liquids but high permeability with respect to gases. For material 50, examples include decontaminated syringe outer tubes and the like for use in pre-filled syringes and the like.

Figure 3:
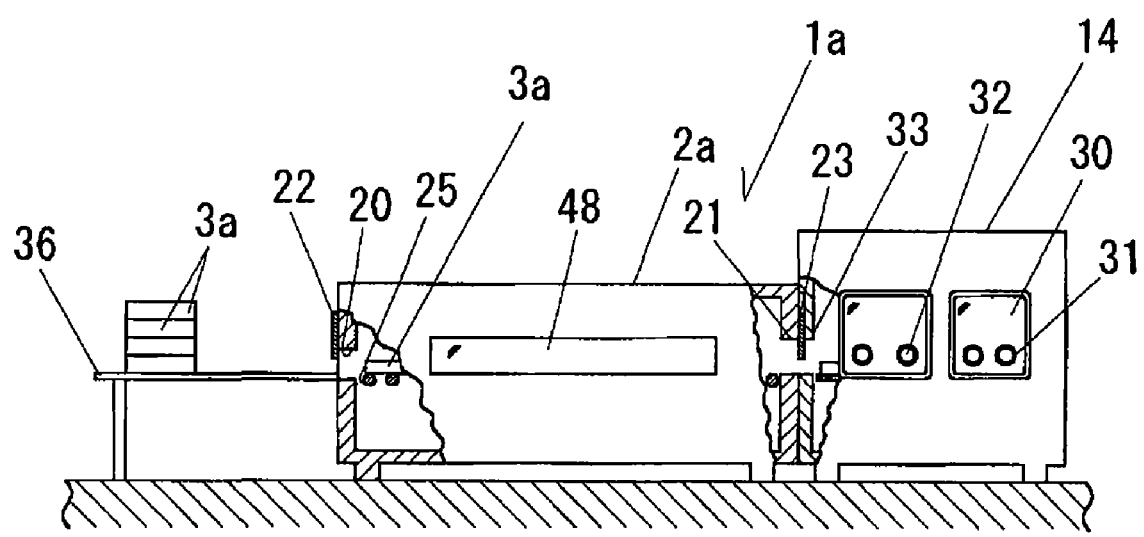
FIG. 3 is a side view of a decontamination apparatus according to another embodiment of the present invention.

Referring to FIG. 3, decontamination apparatus 1a has a hermetically sealed decontamination chamber 2a. In addition, a supply opening 20 and discharge opening 21 are formed on the wall surfaces of hermetically sealed decontamination chamber 2a. Supply opening 20 and discharge opening 21 are opposite each other. Decontamination subject 3a is supplied to the inside of hermetically sealed decontamination chamber 2a from supply opening 20. After decontaminating decontamination subject 3a inside hermetically sealed decontamination chamber 2a at a SAL (sterility assurance level) of $10^{-4}$ to $10^{-12}$, the decontaminated decontamination subject 3a is discharged from discharge opening 21.

Supply opening 20 has a supply opening door 22. Supply opening door 22 moves up and down in order to isolate the inside of the chamber from the outside. Discharge opening 21 has a discharge opening door 23. Discharge opening door 23 is the same mechanism as supply opening door 22. Between the outer wall of hermetically sealed decontamination chamber 2a and the inside surface of each door 22, 23, there is a filler (not shown). As a result, when both doors are shut, the inside of the hermetically sealed decontamination chamber 2a is hermetically isolated from the outside. This door mechanism uses the known art.

Figure 4:
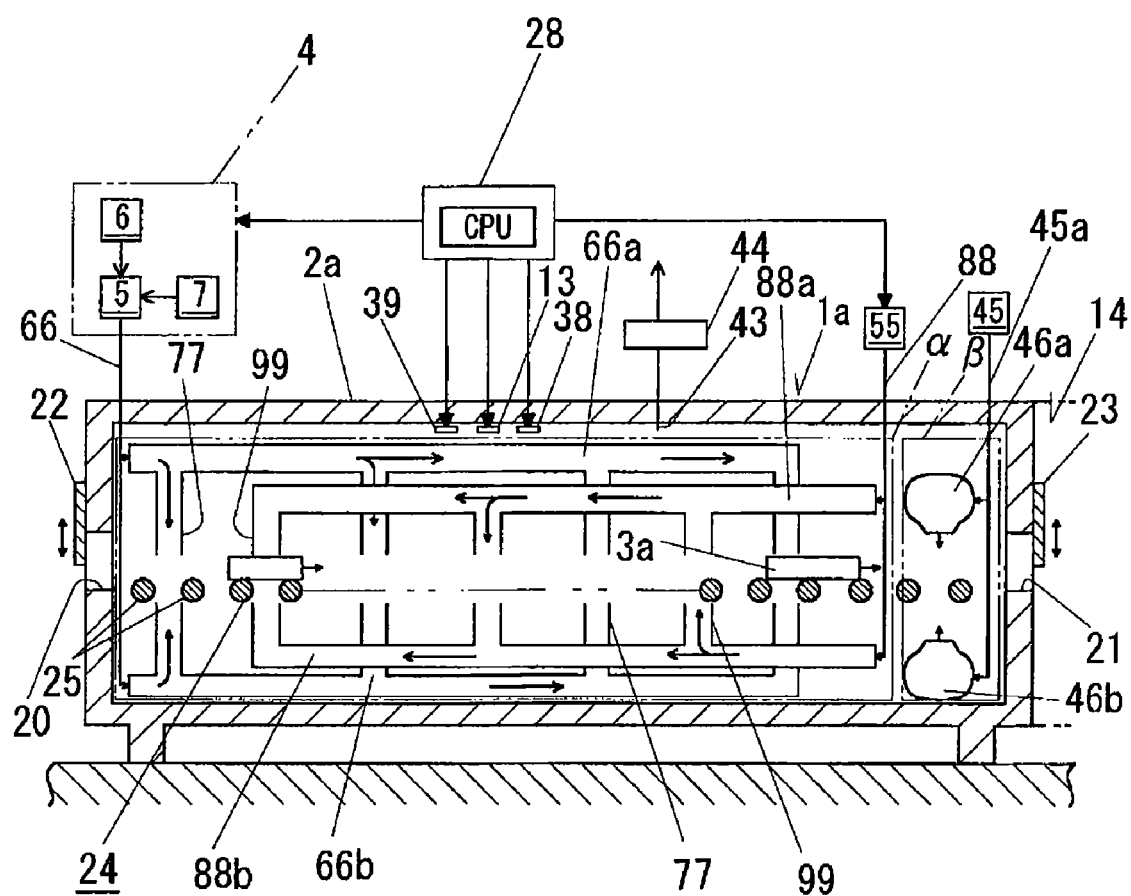
FIG. 4 is a longitudinal side view of a hermetically sealed decontamination chamber of the decontamination apparatus shown in FIG. 3.

In addition, as shown in FIG. 4, in the center of the chamber of hermetically sealed decontamination chamber 2a, a transport apparatus 24 is provided. Transport apparatus 24 is equipped with a plurality of transport rollers 25. Described further, a plurality of cylindrical transport rollers 25 are provided in a row so that the length direction of rollers 25 and the depth of hermetically sealed decontamination chamber 2a are orthogonal. Rollers 25 construct the transport route which connects supply opening 20 and discharge opening 21. In addition, the position of transport rollers 25 is approximately along the same line as an imaginary line connecting the lower rim of supply opening 20 and the lower rim of discharge opening 21. Furthermore, transport roller 25 is axle-supported at prescribed intervals from supply opening 20 to discharge opening 21. The rotation of transport rollers 25 can be controlled. With this embodiment, when decontamination subject 3a is supplied from supply opening 20, decontamination subject 3a is moved on top of transport rollers 25 and transported to discharge opening 21. The transport means of the present invention is constructed with this transport apparatus 24.

In addition, as shown in FIG. 4, hermetically sealed decontamination chamber 2a has a gas generating apparatus 4. Gas generating apparatus 4 is equipped with an evaporator 5, liquid tank 6, and a blower fan 7. Liquid tank 6 contains aqueous hydrogen peroxide in which hydrogen peroxide, which has a higher boiling point than water, is dissolved. When the aqueous hydrogen peroxide is dripped onto a heating surface (not shown) of evaporator 5 by gravity, hydrogen peroxide gas is generated. This hydrogen peroxide gas is sent by blower fan 7 into hermetically sealed decontamination chamber 2a. Hydrogen peroxide gas is sent into hermetically sealed decontamination chamber 2a via decontamination lead-in gas pipe 66. One end of the decontamination lead-in gas pipe 66 is connected to evaporator 5, and the other end is connected to hermetically sealed decontamination chamber 2a. Evaporator 5 has a construction of generating gas by flash evaporation (so-called rapid evaporation method).

Gas generating apparatus 4 can be attached unitarily to hermetically sealed decontamination chamber 2a, or it can be separate. For gas generating apparatus 4, known examples are used.

In addition, inside hermetically sealed decontamination chamber 2a, there are decontamination gas release pipes 66a, 66b which are connected to decontamination gas lead-in pipe 66. Decontamination gas release pipes 66a, 66b are placed along the transport route. Gas release pipes 66a, 66b releases the hydrogen peroxide gas generated by gas generating apparatus 4 inside hermetically sealed decontamination chamber 2a. Described in further detail, first decontamination gas release pipe 66a is placed at an upper position inside hermetically sealed decontamination chamber 2a, and second decontamination gas release pipe 66b is placed in a lower position within the chamber. In addition, both decontamination gas release pipes 66a, 66b have a plurality of decontamination gas release openings 77. Decontamination gas release openings 77 are opened lengthwise on decontamination release pipes 66a, 66b. In addition, the open surface of decontamination gas release opening 77 is placed opposite the outer surface (upper surface and lower surface) of decontamination subject 3a. With this, the hydrogen peroxide gas supplied from decontamination gas lead-in pipe 66 is released towards decontamination subject 3a.

There is also proposed an embodiment in which, in addition to first and second gas release pipes 66a, 66b, a decontamination gas release pipe is placed at side positions inside hermetically sealed decontamination chamber 2a. In other words, this is an embodiment in which the hydrogen peroxide gas is released from top and bottom and left and right. Gas generating apparatus 4, decontamination gas lead-in pipe 66, and decontamination gas release pipes 66a, 66b construct the decontamination gas supply means of the present invention.

Furthermore, decontamination apparatus 1a is equipped with a low humidity gas supply apparatus 55. Low humidity gas supply apparatus 55 brings in low humidity gas into hermetically sealed decontamination chamber 2a. This low humidity gas is sent inside hermetically sealed decontamination chamber 2a by low humidity gas lead-in pipe 88. One end of low humidity gas lead-in pipe 88 is connected to low humidity gas supply apparatus 55, and the other end is connected to hermetically sealed decontamination chamber 2a. In addition, low humidity gas lead-in pipe 88 is connected with low humidity gas release pipes 88a, 88b. Low humidity gas release pipe 88a, 88b are placed inside hermetically sealed decontamination chamber 2a. A plurality of low humidity gas release openings 99 are opened in low humidity gas release pipes 88a, 88b inside hermetically sealed decontamination chamber 2a. Low humidity gas release openings 99 are opened along the length of low humidity gas release pipes 88a, 88b. In addition, the open surface of low humidity gas release opening 99 is placed opposite the outer surface of decontamination subject 3a (upper surface and lower surface). Low humidity gas is supplied to the inside of hermetically sealed decontamination chamber through low humidity gas lead-in pipe 88 and low humidity gas release pipes 88a, 88b, and through low humidity gas opening 99, and this is released at decontamination subject 3a. Low humidity gas release pipes 88a, 88b are constructed from a first low humidity gas release pipe 88a and a second low humidity gas release pipe 88b. First low humidity gas release pipe 88a is placed at a high position inside hermetically sealed decontamination chamber 2a, and in contrast, second low humidity gas release pipe 88b is placed at a low position. With this, low humidity gas is released at the upper and lower surfaces of decontamination subject 3a. A low humidity gas release pipe may be placed at side positions inside hermetically sealed decontamination chamber 2a. With this embodiment, low humidity gas is released from above and below and left and right.

The low humidity gas described above is an unsaturated gas which does not saturate inside the hermetically sealed decontamination chamber 2a. In addition, it is set at a lower humidity than the humidity inside hermetically sealed decontamination chamber 2a. Low humidity gas supply apparatus 55, low humidity gas release pipes 88a, 88b, and low humidity gas lead-in pipe 88 construct the unsaturated gas supply means of the present invention.

Decontamination gas release opening 77 and low humidity gas release opening 99 are formed alternately along the transport route. In addition, their interval is of equal interval of a specified length.

Decontamination gas release pipes 66a, 66b, and low humidity gas release pipes 88a, 88b are placed closer towards supply opening 20 inside hermetically sealed decontamination chamber 2a. Therefore, of the transport route formed inside hermetically sealed decontamination chamber 2a, the earlier part (the space closer to supply opening 20) is a decontamination region alpha for decontaminating decontamination subject 3a. In contrast, the later part of the transport route (the space closer to discharge opening 21), is an aeration region beta for removing condensed liquid layer m of decontamination subject 3a. Therefore, the description up until now has mainly been a description of decontamination region alpha.

In this manner, decontamination apparatus 1a of the present invention divides a single space (hermetically sealed decontamination chamber 2a) into two, and in the earlier stage, decontamination region alpha is formed, and in the later stage, aeration region beta is formed.

Next, aeration region beta is described.

Aeration region beta is provided with a first louver 46a and a second louver 46b. Hot air is released from first louver 46a and second louver 46b. In addition, first louver 46a is positioned higher than transport roller 25. Therefore, first louver 46a releases hot air onto the upper surface of decontamination subject 3a. In contrast second louver 46b is positioned lower than transport roller 25. Therefore, second louver 46b releases hot air onto the lower surface of decontamination subject 3a. In addition, this hot air is supplied from a hot air supply apparatus 45 via a hot air lead-in pipe 45a. Hot air supply apparatus 45 is provided outside hermetically sealed decontamination chamber 2a. The condensed liquid layer removal means of the present invention is constructed from hot air supply apparatus 45, hot air lead-in pipe 45a, and louvers 46a, 46b.

Decontamination apparatus 1a is also equipped with a control part 28. Control part 28 is equipped with a central control apparatus CPU. Central control apparatus CPU is connected electrically with gas generating apparatus 4, low humidity gas supply apparatus 55, and hot air supply apparatus 45. Control part 28 exchanges specific data with each apparatus and the like and controls each apparatus 4, 55, 45. With regard to the control content of central control apparatus CPU, this will be described later.

In addition, decontamination apparatus 1a is equipped with a temperature detection apparatus 38 and a humidity detection apparatus 39. Temperature detection apparatus 38 and humidity detection apparatus 39 detects the temperature and humidity of hermetically sealed decontamination chamber 2a. In addition temperature detection apparatus 38 and humidity detection apparatus 39 are each electrically connected to the central control apparatus CPU. The detection data of temperature detection apparatus 38 and humidity detection apparatus 39 is transmitted to central control apparatus CPU. The condensation control means of the present invention is constructed from control part 28, gas generating apparatus 4, low humidity gas supply apparatus 55, temperature detection apparatus 38 and humidity detection apparatus 39 of the present embodiment.

Furthermore, decontamination apparatus 1a is equipped with an inner pressure regulator 13. Inner pressure regulator 13 adjusts the inner pressure of hermetically sealed decontamination chamber 2a. Furthermore, inner pressure regulator 13 is connected to central control apparatus CPU. Central control apparatus CPU uses inner pressure regulator 13 to have, at prescribed times, a higher pressure inside hermetically sealed decontamination chamber 2a than the outside.

In addition, a gas exhaust opening 43 is opened inside hermetically sealed decontamination chamber 2a. Gas exhaust opening 43 exhausts the gas inside hermetically sealed decontamination chamber 2a at the time of aeration. When gas is exhausted, the hydrogen peroxide component of the gas inside hermetically sealed decontamination chamber 2a is decomposed by a catalyst 44 and exhausted to the outside.

On the wall surface of hermetically sealed decontamination chamber 2a, a transparent window 48 for the hermetically sealed chamber is formed. Transparent window 48 for the hermetically sealed chamber is of a glass material or the like. With this, the worker can see the inside of hermetically sealed decontamination chamber 2a through transparent window 48 for the hermetically sealed chamber.

Figure 6:
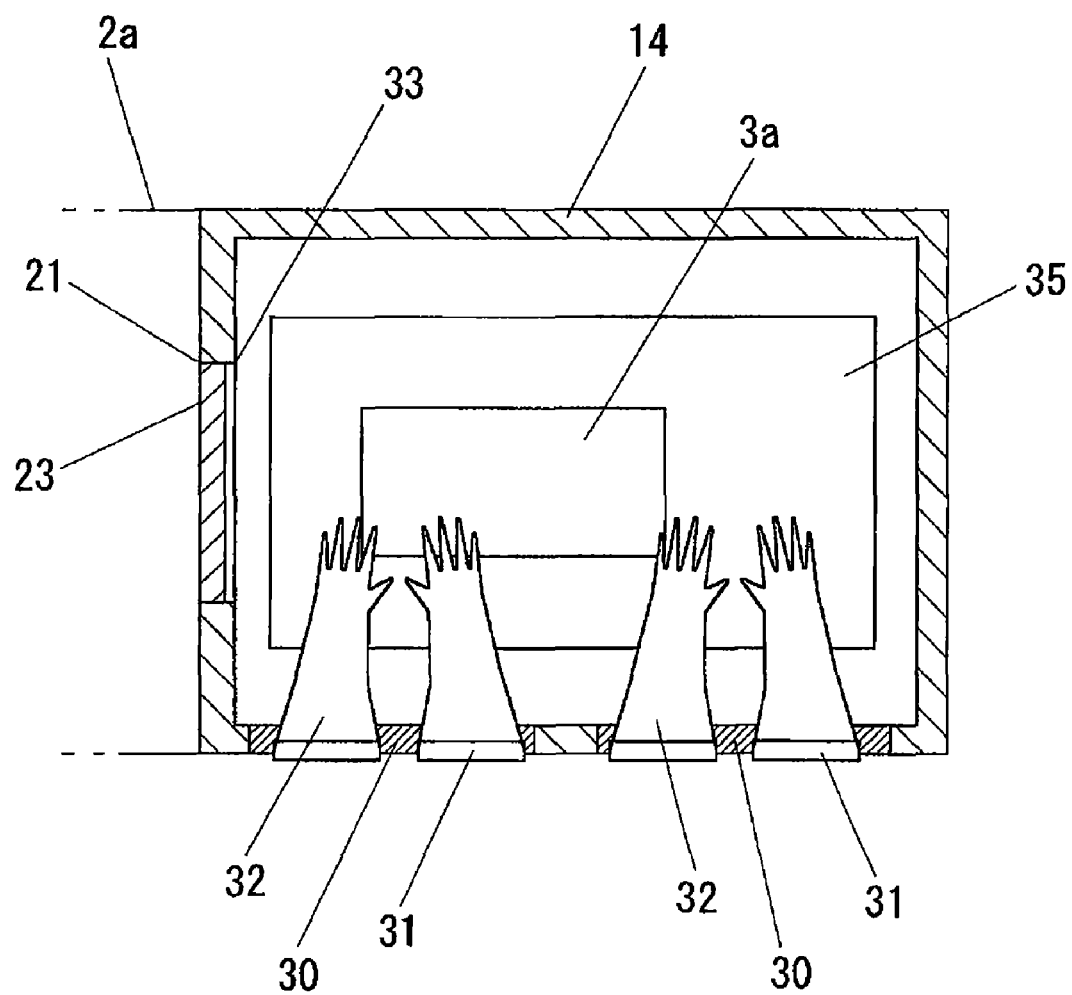
FIG. 6 is a transverse plan view of an isolator of the decontamination apparatus according shown in FIG. 3.

Furthermore, as shown in FIGS. 3 and 6, decontamination apparatus 1a is equipped with an isolator which is connected with hermetically sealed decontamination chamber 2a. On the wall surface of isolator 14 that is closer towards hermetically sealed decontamination chamber 2a, there is a communication opening 33. Communication opening 33 is connected with discharge opening 21 of hermetically sealed decontamination chamber 2a. Both chambers are connected via communication opening 33 and discharge opening 21. With this, decontamination subject 3a inside hermetically sealed decontamination chamber 2a is directly transported to the inside of isolator 14. When discharge opening door 23 is shut, both chambers are hermetically isolated. In other words, hermetically sealed decontamination chamber 2a and isolator 14 are hermetically connected. Therefore, contaminated gas does not enter inside hermetically sealed decontamination chamber 2a from the outside. Known art can be suitably used for the connection mechanism.

In addition, isolator 14, as shown in FIG. 6, is provided with a removal means for removing wrapping material 51 of decontamination subject 3a. The removal means is work gloves 32. Stated more concretely, on the wall surface of isolator 14, there is a glass window 30. Furthermore, there are work holes 31 formed on glass window 30. The base end of work gloves 32 is hermetically attached to work holes 31.

After decontaminating decontamination subject 3a in hermetically sealed decontamination chamber 2a, decontamination subject 3a is transported directly to isolator 14. A work table 35, on which the transported decontamination subject 3a from hermetically sealed decontamination chamber 2a is placed, is placed at the center of isolator 14. The transported decontamination subject 3a is placed on top of work table 35. When hands are inserted into work gloves 32, while confirming decontamination subject 3a through glass window 30, inside work is conducted. The wrapping material removal chamber of the present invention is constructed from isolator 14.

Next, the decontamination method using decontamination apparatus 1a is described.

First, supply opening door 22 and discharge opening door 23 are shut, and the inside of hermetically sealed decontamination chamber 2a is hermetically isolated from the outside. Next, by driving low humidity gas supply apparatus 55, low humidity gas is released inside hermetically sealed decontamination chamber 2a, and humidity adjustment inside hermetically sealed decontamination chamber 2a is conducted. In this way, the humidity adjustment inside hermetically sealed decontamination chamber 2a is conducted in advance in order to heighten the concentration of hydrogen peroxide gas inside hermetically sealed decontamination chamber 2a and to stabilize this concentration. When the humidity inside hermetically sealed decontamination chamber 2a reaches a prescribed humidity, the charging of low humidity gas is stopped.

Decontamination subject 3a is collected on top of collection table 36 (see FIG. 1) which is placed before supply opening 20 of hermetically sealed decontamination chamber 2a. Supply opening door 22 is opened, and the collected decontamination subjects 3a are supplied to hermetically sealed decontamination chamber 2a from supply opening 20. At this time, decontamination subject 3a is still wrapped in wrapping material 51. In addition, when supply opening door 22 is opened, inner pressure regulator 13 is controlled so that the inner pressure inside hermetically sealed decontamination chamber 2a is pressurized as compared to the outside atmosphere. With this, when decontamination subject 3a is supplied to hermetically sealed decontamination chamber 3a, contaminants are prevented from entering supply opening 20.

Figure 7:
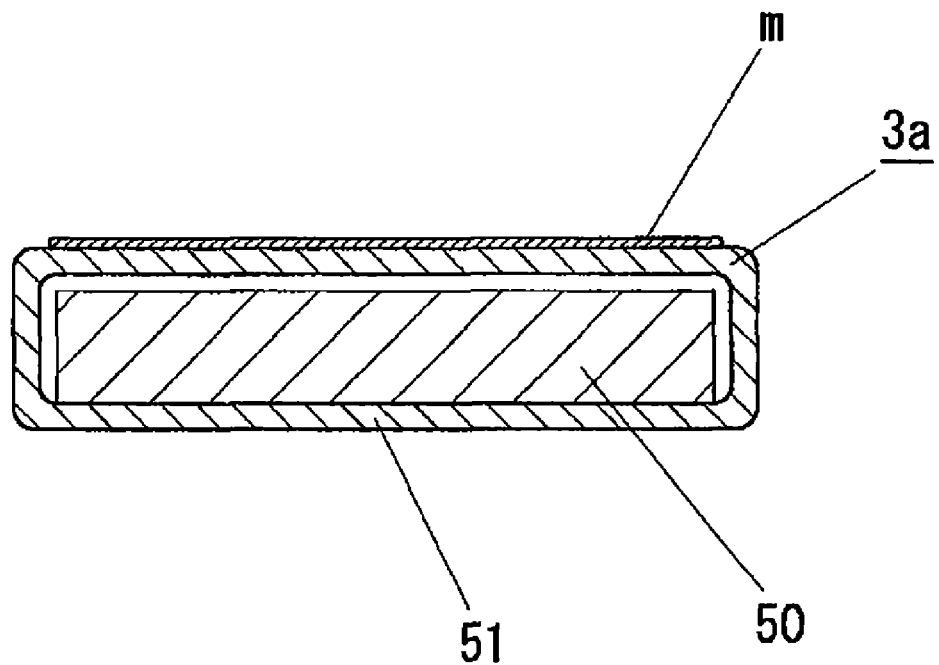
FIG. 7 is a longitudinal side view of a decontamination subject according to the present invention, in which a condensed liquid layer is formed on a wrapping material.

When decontamination subject 3a is supplied to the inside of hermetically sealed decontamination chamber 2a, supply opening door 22 is shut. Next, the charging of hydrogen peroxide gas to inside hermetically sealed decontamination chamber 2a is initiated. With this, transport apparatus 24 is started, and at a prescribed speed, decontamination subject 3a is transported along the transport route. Furthermore, low humidity gas supply apparatus 55 is also started. Supply opening door 22, discharge opening door 23, and transport apparatus 24 are each connected to central control apparatus CPU (not shown). Therefore, supply opening door 22, discharge opening door 23, and transport apparatus 24 are controlled by control part in a unified manner. In addition, central control apparatus CPU controls gas generating apparatus 4, low humidity gas supply apparatus 55, humidity detection apparatus 38, and humidity detection apparatus 39 according to an operational program determined in advance. Stated more concretely, a control content is determined in advance in which a prescribed amount of hydrogen peroxide gas is charged inside hermetically sealed decontamination chamber 2a, and a condensed liquid layer m (see FIG. 7) is formed as a thin film on the outer surface of wrapping material 51.

Decontamination subject 3a moves along the transport route by transport apparatus 24. Hydrogen peroxide gas and low humidity gas are alternately released. This is because the release openings 77, 99 are placed alternately. If, while decontamination subject 3a proceeds on the transport route, hydrogen peroxide gas is released, a condensed liquid layer m is formed on the outer surface of decontamination subject 3a. If low humidity gas is released, condensed liquid layer m is evaporated. Therefore, a condensed liquid layer m is alternately formed and evaporated on the outer surface of decontamination subject 3a which is being transported in the early stage of the transport route (in other words, decontamination region alpha). This is described in further detail below.

In the transport process of decontamination subject 3a, when decontamination subject 3a is positioned in the region sandwiched between decontamination gas release openings 77 formed on top and bottom, hydrogen peroxide gas is released onto the outer surface of decontamination subject 3, and a condensed liquid layer m is formed.

Decontamination subject 3a is moved further, and when decontamination subject 3a is positioned in the region sandwiched between low humidity gas release openings 99, low humidity gas is released on the outer surface of decontamination subject 3a. With this, the condensed liquid layer m that has been formed begins to partially evaporate (evaporation process). At this time, the hydrogen peroxide gas has a boiling point of 150 degrees C. which is a higher boiling point than water, and the water contained in condensed liquid layer m vaporizes before hydrogen peroxide. As a result, the hydrogen peroxide concentration of condensed liquid layer m becomes higher. When low humidity gas is further released, the condensed liquid layer m begins to evaporate wholly. With this, by wholly evaporating the condensed liquid layer m that has been formed within a prescribed time, the condensed liquid of condensed liquid layer m is prevented from becoming a gas, and this hydrogen peroxide gas is prevented from penetrating wrapping material 51. The prescribed time is a time which is shorter than the time needed for the condensed liquid of condensed liquid layer m to become a gas to penetrate the wrapping material and reach the material on the inside. This time, and also taking into consideration the interval of release openings 77, 99, is realized by prescribing an appropriate transport speed.

When decontamination subject 3a is transported further and is positioned at a region sandwiched between decontamination gas release openings 77, the condensed liquid layer m is re-formed on the outer surface of wrapping material 51 (re-condensation process). Decontamination is implemented again.

In this way, when the evaporation step and the re-condensation step are repeatedly implemented, the penetration of the decontamination components to material 50 is prevented. Material 50 is not deteriorated, and a high concentration condensed liquid layer m is maintained for a long period of time.

Next, the decontamination subject 3a which passes through decontamination subject alpha is transported to aeration region beta which is the later stage of the transport route. Here, condensed liquid layer m remaining on the outer surface of decontamination subject 3a is removed, and aeration is implemented. Described in further detail, decontamination subject is transported by transport rollers 25, and it is positioned in a region sandwiched between louvers 46a, 46b. Hot air (40 degrees C. to 150 degrees C.) is sprayed out from top and bottom onto the outer surface of decontamination subject 3a which has already been decontaminated. With this, any condensed liquid layer m remaining on the outer surface and any surrounding hydrogen peroxide gas is removed. Therefore, after decontamination, aeration is implemented with regard to decontamination subject 3a. Each of louvers 46a, 46b is placed so that the release direction is towards decontamination subject 3a. This embodiment does not impede the decontamination effect.

After aeration is completed, discharge opening door 23 is opened. Decontamination subject 3a is transported to isolator 14 from discharge opening 21. Here also, as described above, the inner pressure inside hermetically sealed decontamination chamber 2a is higher than the inner pressure of isolator 14. With this, contamination of the inside of hermetically sealed decontamination chamber 2a is prevented. After transporting decontamination subject 3a to isolator 14, discharge opening door 23 is shut. Next, inside isolator 14, wrapping material 51 of decontamination subject 3a is removed using work gloves 32. The material 50 inside is taken out. With this, various operations can be conducted with isolator 14.

As described up to now, the early stage of the transport route is a decontamination region alpha and the later stage is an aeration region beta. In the first half of the transport process, decontamination is implemented, and in the later stage, aeration is implemented. With this embodiment, the entire region of the hermetically sealed decontamination chamber 2a does not need to be aerated. In addition, decontamination subject 3a does not need to be held for a period of time inside hermetically sealed decontamination chamber for aeration. As a result, the aeration time is shortened. Therefore, decontamination subject 3a can be supplied one after the other to the inside of hermetically sealed decontamination chamber 2a, and the rotation timing for the transport roller 25 and the timing for opening and closing both doors 22, 23 are in concert with this, and the same number as the number supplied is transported to isolator 14. This process is a continuous flow, and a continuous decontamination operation is implemented. With this, the overall decontamination time is dramatically shortened. Furthermore, a plurality of decontamination subjects 3a can have approximately the same interval as the intervals for release openings 77, 99, and the transport apparatus 24 transports through intermittent operation. This is because the plurality of decontamination subjects 3a is decontaminated simultaneously in parallel in the early stage of the transport route. This embodiment dramatically improves the decontamination efficiency. In this way, transport apparatus 24 intermittently drives transport roller 25, and decontamination subject 3a is transported intermittently. This is preferred because at each position that the decontamination subject is placed, an adequate time for condensed liquid layer formation or removal is possible. In the present invention, this does not preclude an embodiment in which decontamination subject 3a is continuously transported.

Furthermore, in aeration region beta, this can have an embodiment having an apparatus for spraying steam. Described in further detail, with decontamination apparatus 1a, after spraying steam onto the outer surface of wrapping material 51 of decontamination subject 3a, the aqueous hydrogen peroxide remaining on the outer surface is masked and the hydrogen peroxide gas concentration in isolator 14 is apparently reduced.

In addition, this can be an embodiment in which low humidity gas is sprayed. Low humidity gas is a gas with a prescribed humidity that is below the humidity of aeration region beta. With this, the condensed liquid layer m which remains on the outer surface and the hydrogen peroxide gas in the periphery are removed. With this embodiment, the low humidity gas apparatus 55 can be shared with decontamination region alpha.

Figure 5:
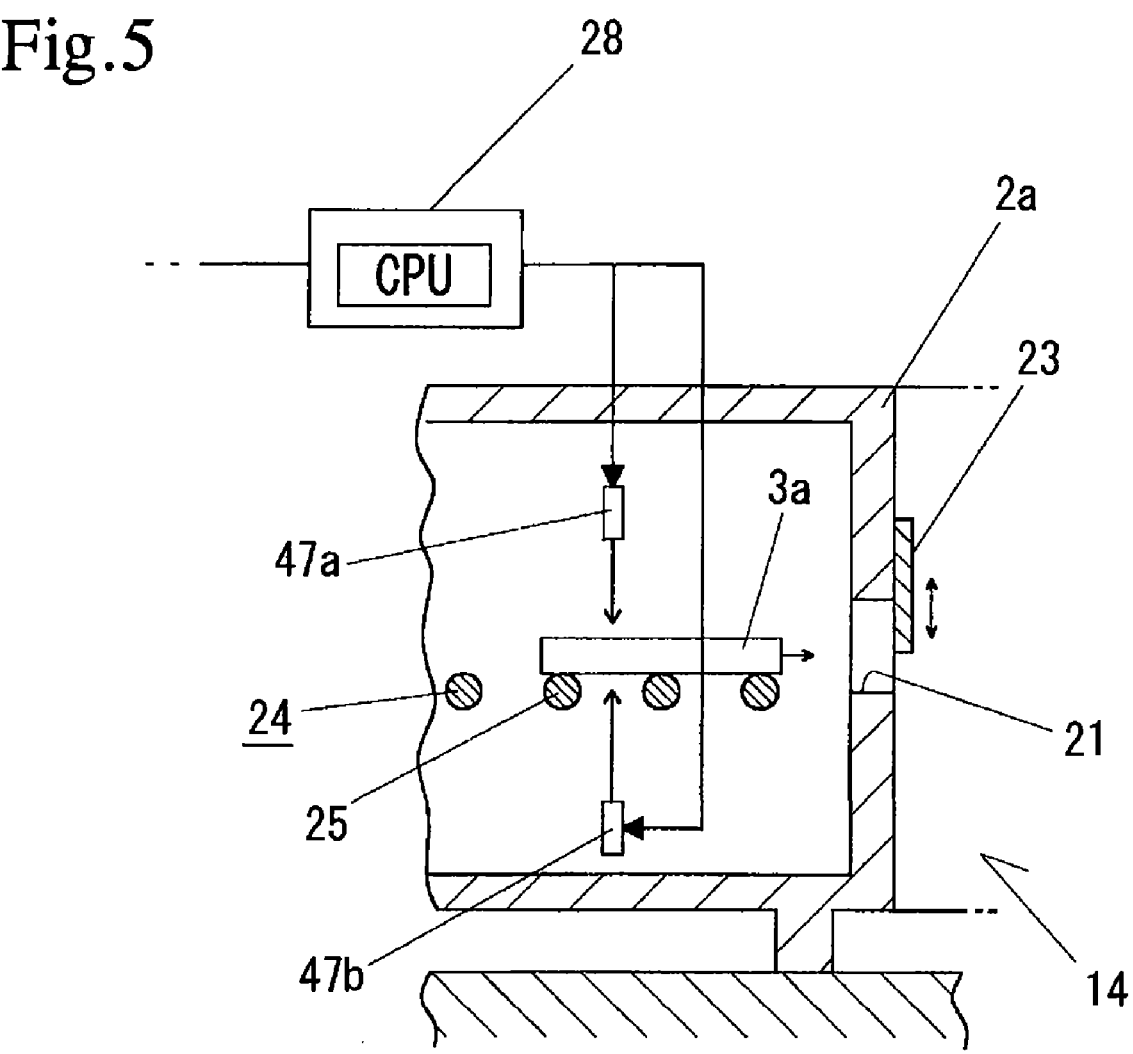
FIG. 5 is a longitudinal side view of the hermetically sealed decontamination chamber provided with louvers.

Furthermore, as shown in FIG. 5, as another embodiment, there is an embodiment in which aeration region beta is provided with a UV irradiation apparatus 47a, 47b. Described in further detail, UV irradiation apparatus 47a, 47b are constructed from a first UV irradiation apparatus 47a and a second UV irradiation apparatus 47b. First UV irradiation apparatus 47a is placed at a high position inside the chamber. In contrast, second UV irradiation apparatus 47b is placed in a lower position inside the chamber. Therefore, the outer surface of decontamination subject 3a which has been transported by transport rollers 25 is irradiated by ultraviolet (180 nm–400 nm) from the top and bottom. With this, the decontamination subject 3a which has been decontaminated is aerated by decomposing the condensed liquid layer m formed on the outer surface of decontamination subject 3a and hydrogen peroxide gas in the periphery.

With the embodiment in which hot air is sprayed, the embodiment in which steam is sprayed, the embodiment in which low humidity gas is sprayed, and the embodiment in which there is UV radiation, these embodiments can be variously combined. In addition, the known technology can be used for the aeration conditions.

In the present invention, a hermetically sealed decontamination chamber 2a has, on a chamber wall, a supply opening 20 for supplying a decontamination subject 3a from outside the chamber to inside the chamber and a discharge opening 21 for discharging the decontamination subject 3a from inside the chamber to outside the chamber, and when supply opening 20 and discharge opening 21 are shut, the inside of the chamber is hermetically isolated from the outside. Hermetically sealed decontamination chamber 2a is charged with hydrogen peroxide gas, and the hydrogen peroxide gas is condensed inside the hermetically sealed decontamination chamber so that a thin-film condensed liquid layer m is formed on an outer surface of decontamination subject 3a. After a prescribed amount of time from the time of formation, an evaporation process is implemented, and after implementing the evaporation process, a re-condensation process is implemented. After implementing the re-condensation process, condensed liquid layer m that has been formed is removed, and decontamination subject 3a is discharged from discharge opening 21. In addition, when realizing this decontamination method, there is proposed an embodiment in which hermetically sealed decontamination chamber is not provided with transport apparatus 24.

In addition, for the decontamination gas for implementing the decontamination process comprising the evaporation process and the re-condensation process, any decontamination gas which has a higher boiling point than water is used with good results. In addition, for the decontamination gas, gases of decontaminating agents such as formaldehyde, ethylene oxide, aqueous acetyl hydroperoxide, and ozone water, and the like can be used.

In addition, an embodiment of decontamination subject 3a is not limited to that of decontamination subject 3a that has been described.

Obviously, numerous modifications and variations of the present invention are possible in light of the above teachings. It is therefore to be understood that within the scope of the appended claims, the invention may be practiced otherwise than as specifically described herein.

What is claimed is:

1. A method of decontamination, comprising the steps of:
generating a decontamination gas by evaporating an aqueous solution in which the decontamination gas with a higher boiling point than water is dissolved;
charging the decontamination gas into a hermetically sealed decontamination chamber;
condensing the decontamination gas in the hermetically sealed decontamination chamber;
forming a condensed liquid layer in a form of a thin film on an outer surface of a decontamination subject in the hermetically sealed decontamination chamber;
evaporating the condensed liquid layer at least partially by supplying unsaturated gas into the hermetically sealed decontamination chamber, the unsaturated gas not saturating in the hermetically sealed decontamination chamber; and
re-condensing the decontamination gas after the evaporating step to re-form the condensed liquid layer, by closing supply of the unsaturated gas and re-charging the decontamination gas into the hermetically sealed decontamination chamber.

2. The method of decontamination according to claim 1, wherein the re-condensing step is performed a plurality of times.

3. The method of decontamination according to claim 1, wherein the decontamination gas is hydrogen peroxide gas.

4. A method of decontamination, comprising the steps of:
providing a chamber with a chamber wall having a supply opening to supply a decontamination subject into the chamber, and a discharge opening to discharge the decontamination subject from the chamber after being decontaminated;
supplying the decontamination subject into the chamber through the supply opening;
closing the supply opening and the discharge opening to turn the chamber to a hermetically sealed decontamination chamber with the decontamination subject inside;
charging decontamination gas into the hermetically sealed decontamination chamber;
condensing the decontamination gas in the hermetically sealed decontamination chamber;
forming a condensed liquid layer in a form of a thin film on an outer surface of the decontamination subject so as to decontaminate the decontamination subject;

evaporating the condensed liquid layer at least partially by supplying unsaturated gas into the hermetically sealed decontamination chamber;

re-condensing the decontamination gas after the evaporating step to re-form the condensed liquid layer, by closing supply of the unsaturated gas and re-charging the decontamination gas into the hermetically sealed decontamination chamber;

removing the condensed liquid layer re-formed on the outer surface of the decontamination subject; and discharging the decontamination subject through the discharge opening, wherein the forming step is performed during a first half of the steps beginning the supplying step and ending the discharging step, the evaporating step is performed when a predetermined period of time is passed after the condensed liquid layer is formed in the forming step, and the removing step is performed during a second half of the steps beginning the supplying step and ending the discharging step.

5. The method of decontamination according to claim 4, wherein an inner pressure of the hermetically sealed decontamination chamber is higher than outside atmosphere when inside of the hermetically sealed decontamination chamber is in communication with outside of the hermetically sealed decontamination chamber.

6. The method of decontamination according to claim 4, wherein the decontamination subject includes a decontaminated material wrapped with a wrapping material while the decontaminated material is maintained sterile.

7. The method of decontamination according to claim 6, further comprising the steps of:

providing a wrapping material removal chamber inside of which being decontaminated and being in communication with inside of the hermetically sealed decontamination chamber;

closing the communication between the hermetically sealed decontamination chamber and the wrapping material removal chamber prior to the supplying step; and opening the communication between the hermetically sealed decontamination chamber and the wrapping material removal chamber after the removing step, wherein in the discharging step, the decontamination subject is discharged through the discharge opening into the wrapping material removal chamber, and the wrapping material of the decontamination subject is removed in the wrapping material removal chamber from the decontaminated material after closing the communication between the hermetically sealed decontamination chamber and the wrapping material removal chamber.

8. The method of decontamination according to claim 4, wherein the decontamination gas is hydrogen peroxide gas.

9. A decontamination apparatus comprising:

a chamber having a chamber wall provided with a supply opening to supply a decontamination subject into the chamber, and a discharge opening to discharge the decontamination subject from the chamber after being decontaminated, the chamber being turned to a hermetically sealed decontamination chamber when the supply opening and the discharge opening are closed;

a decontamination gas supplying device provided with a decontamination gas release opening facing oppositely to an outer surface of the decontamination subject in the chamber, and configured to release decontamination gas toward the decontamination subject through the decontamination gas release opening, the decontamination gas being generated by evaporating an aqueous solution in which the decontamination gas with a higher boiling point than water is dissolved;

an unsaturated gas supplying device provided with an unsaturated gas release opening facing oppositely to the outer surface of the decontamination subject, and configured to generate and release unsaturated gas toward the decontamination subject through the unsaturated gas release opening, the unsaturated gas not saturating in the hermetically sealed decontamination chamber;

a condensation controlling device configured to condense the decontamination gas released in the hermetically sealed decontamination chamber, to form a condensed liquid layer in a form of a thin film on the outer surface of the decontamination subject, and to decontaminate the decontamination subject; and a removing device configured to remove the condensed liquid layer from the decontamination subject.

10. The decontamination apparatus according to claim 9, further comprising:

a transporting device provided in the hermetically sealed decontamination chamber, and configured to transport the decontamination subject supplied through the supply opening to the discharge opening along a transport route having a first stage and a second stage, wherein the decontamination gas supplying device includes a plurality of decontamination gas release openings through which the decontamination gas is released toward the decontamination subject while being transported along the first stage of the transport route, the unsaturated gas supplying device includes a plurality of unsaturated gas release openings, the removing device removes the condensed liquid layer from the decontamination subject while being transported along the second stage of the transport route, and the decontamination gas release openings and the unsaturated gas release openings are provided alternately along the first stage of the transport route.

11. The decontamination apparatus according to claim 10, wherein:

the decontamination gas release openings and the unsaturated gas release openings are provided alternately at an interval; and the transporting device transports a plurality of decontamination subjects along the transport route at a substantially same interval as the interval for the decontamination gas release openings and the unsaturated gas release openings.

12. The decontamination apparatus according to claim 10, wherein the decontamination subject includes a decontaminated material wrapped with a wrapping material while the decontaminated material is maintained sterile.

13. The decontamination apparatus according to claim 9, further comprising:

a wrapping material removal chamber provided with a communication opening that connects with the discharge opening of the chamber and communicates with the chamber through the communication opening; and inside of the wrapping material removal chamber is decontaminated.

14. The decontamination apparatus according to claim 9, wherein the decontamination gas is hydrogen peroxide gas.

* * * * *